US00PP14388P29

(12) United States Plant Patent
Berry

(10) Patent No.: US PP14,388 P2
(45) Date of Patent: Dec. 16, 2003

(54) *RAPHIOLEPIS INDICA* PLANT NAMED 'SOPINK'

(50) Latin Name: *Raphiolepis indica*
Varietal Denomination: Sopink

(75) Inventor: James Bryan Berry, Daphne, AL (US)

(73) Assignee: Plant Development Services, Inc., Loxley, AL (US)

( * ) Notice: Subject to any disclaimer, the term of this patent is extended or adjusted under 35 U.S.C. 154(b) by 0 days.

(21) Appl. No.: 10/370,764

(22) Filed: Feb. 24, 2003

(51) Int. Cl.[7] ..... A01H 5/00
(52) U.S. Cl. ..... Plt./254
(58) Field of Search ..... Plt./254

*Primary Examiner*—Kent Bell

(57) ABSTRACT

A new and distinct variety of *Raphiolepis indica* found as an openly pollinated seedling of *Raphiolepis indica* 'Snow White'. The new variety is unique with its dense, mounding growth habit, moderate to fast growth rate, and attractive single to semi-double pink flowers.

2 Drawing Sheets

BACKGROUND OF THE INVENTION

This new Raphiolepis variety named 'Sopink' was found as an openly pollinated seedling of *Raphiolepis indica* 'Snow White', an unpatented variety, maintained by Plant Development Services Inc. in Loxley, Ala. The seedling, hereinafter referred to as 'Sopink', was discovered by James Bryan Berry in April, 1998. The value of this new cultivar lies in its dense, mounding habit, moderate to fast growth rate, improved resistance to fireblight and leaf spot, and an abundance of pink flower clusters. The new variety has retained many of the outstanding attributes of its parent cultivar, in particular its tolerance of heat, drought, salt, and disease which makes it adaptable to culture in most of the Sunbelt States. As with the parent cultivar, the plant of this invention may be advantageously employed as a specimen appointment, a ground cover, in either formal or informal groupings, and is quite attractive in mass plantings. 'Sopink' serves well in foundation plantings and is adapted for culture as a potted plant. 'Sopink' is responsive to pruning and training and may be employed in forming dense, attractive hedges, and maintained without an excessive amount of care. This plant is easy to care for and maintain in size due to its short internodes, heavy branching, and dense canopy. Its natural propensity to remain small to maturity makes it valuable for landscape uses in smaller home gardens which require plants that do not outgrow their intended mature dimensions.

While evaluating the *Raphiolepis indica* 'Snow White' seedlings, attention was directed toward leaf spot and fireblight resistance. Any of the seedlings which showed susceptibility to either disease were discarded. Most varieties of pink Raphiolepis tend to be susceptible to leaf spot and fireblight; however, this new variety was selected for its resistance to these diseases. As a result, little or no chemical spray is needed which benefits the environment.

Cold-hardiness was also a very important criterion. Plants of this seed group, as well as the parent, were evaluated in Alabama, Georgia, and Florida, during the winters of 1994 and 1995. The new variety, *Raphiolepis indica* 'Sopink' attained high levels of cold-hardiness earlier than the other selections and maintained this level of cold-hardiness throughout the winter and into the early spring.

Asexual propagation of the new plant by cuttings has been under Mr. Berry's direction in Loxley, Ala. The new plant retains its distinctive characteristics and reproduces true to type in successive generations. The plant cannot be reproduced true from seed.

SUMMARY OF THE INVENTION

The following are the most outstanding and distinguishing characteristics of this new cultivar when grown under normal horticultural practices in Loxley, Ala.

1. Dense and mounding in nature. Plant is wider than tall.
2. Moderate to fast growth rate.
3. New growth terminals are pronounced with a light bronze coloration which offers a novel and strikingly appealing contrast of new foliage to old foliage in plants of this market class.
4. Hardy to Zone 7.
5. Heat and drought tolerant.
6. Good plant for coastal areas because of wind and salt tolerance.
7. Has shown good resistance to leaf spot and fireblight.
8. Relatively pest resistant.
9. Good specimen plant.
10. Good foundation plant.
11. Very desirable in planters.
12. Produces seeds and therefore may result in bird visitations.
13. Makes a very good low growing hedge.
14. Flowers are single to semi-double, pink, fragrant, and profuse.

DESCRIPTION OF THE DRAWINGS

This new *Raphiolepis indica* variety is illustrated by the accompanying photographic prints in which:

1. The photograph at the top of the first sheet is a close-up showing the flower, buds, foliage and stem color as well as flower size and form.

2. The photograph at the bottom of the first sheet shows the dense and mounding growth habit of a three gallon plant.
3. The photograph at the top of the second sheet is a side-by-side photograph of (from left to right) *Raphiolepis indica* 'Sopink', *Raphiolepis indica* 'Snow White', and *Raphiolepis indica* 'Conor' U.S. Plant Pat. No. 9,398 in early spring.
4. The photograph at the bottom of the second sheet shows the dense and mounding growth habit of a crop of young three gallon plants.

The colors shown are as true as is reasonably possible to obtain by conventional photographic procedures. Colors in the photographs may appear different than actual colors due to light reflectance. The colors of the various plant parts are defined with reference to The Royal Horticultural Society Colour Chart. Description of colors in ordinary terms are presented where appropriate for clarity in meaning.

BOTANICAL DESCRIPTION OF THE PLANT

The following is a detailed description of the new variety of Raphiolepis based on my observations made of two year old plants grown in three gallon containers in wholesale commercial production practices, in greenhouses, and in established landscape plantings in Loxley, Ala.

Distinctive Characteristics

| Characteristic | *Raphiolepis i.* 'Sopink' | *Raphiolepis i.* 'Snow White' |
|---|---|---|
| Height (Mature) | 3–4' | 3–4' |
| Width (Mature) | 4–5' | 4–5' |
| Leaf Length | 2⅛–2¾" | 2⅛–2¾" |
| Leaf Width | ⅞–1⅜" | ⅞–1⅜" |
| Leaf Margin | Serrate-Crenate | Serrate-Crenate |
| Leaf Tip | Acute | Acute |
| Leaf Curvature | Almost Flat | Almost Flat |
| Flower | Single to Semi-Double | Single |
| Flower Color | Red-Purple G. 65C | White G. 155D |
| Petal Number | 5–9 | 5 |
| Petal Shape | Oblanceolate | Oblanceolate |
| Growth Rate | Moderate–Fast | Moderate–Fast |

| Characteristic | *Raphiolepis i.* 'Conor' PP#9398 | *Raphiolepis i.* The Species |
|---|---|---|
| Height (Mature) | 3–4' | 3–5' |
| Width (Mature) | 4–5' | 3–5' |
| Leaf Length | 2–3" | 1–3" |
| Leaf Width | 1–1¼' | ¾–1½" |
| Leaf Margin | Serrate-Crenate | Entire-Serrate |
| Leaf Tip | Acute | Acute-Obtuse |
| Leaf Curvature | Undulate w/Revolute Margins | Flat-Undulate |
| Flower | Semi-Double | Single to Semi-Double |
| Flower Color | Red-Purple G. 65B | White Pink |
| Petal Number | 5–8 | 5–10 |
| Petal Shape | Oblanceolate | Elliptic-Oblanceolate |
| Growth Rate | Moderate–Slow | Slow–Fast |

*Raphiolepis indica* 'Sopink', *Raphiolepis indica* 'Snow White', and *Raphiolepis indica* 'Conor' are cultivars of Rosaceae *Raphiolepis indica*. The author of the genus name Raphiolepis is John Lindley (1799–1865). The original author of the species name Indica is Carlolus Linnaeus (1707–1778) and the name was transferred to the plant *Raphiolepis indica* by John Lindley.

The new variety 'Sopink' was found in 1998 as an openly pollinated seedling of *Raphiolepis indica* 'Snow White'. It has the Trademark name Snow Pink and is listed as *Raphiolepis indica* Snow Pink™ 'Sopink'.

*Raphiolepis indica* 'Conor' U.S. Plant Pat. No. 9,398 and the non-patented variety *Raphiolepis indica* 'Snow White' are well known in the industry and are comparable to 'Sopink' in that all are compact growers. However, there are many differences. The foliage of 'Conor' has an undulate shape with revolute margins compared to the almost flat foliage of the new variety. The flowers of the new variety are single to semi-double and light pink compared to the 'Snow White' flowers which are single and white.

Classification:
Botanical: *Raphiolepis indica* 'Sopink'.
Parentage: Chance seedling of *Raphiolepis indica* 'Snow White'.
Commercial: Broadleaf evergreen.
Form: Dense and mounding.
Height: 3–4'.
Width: 4–5'.
Growth rate: Moderate to fast under normal fertilization and moisture conditions. Semi-hardwood cuttings taken in late spring and through the summer produce rooted cuttings in three to four months in Loxley, Ala. Root development is vigorous and finely branched. In a period of four years from a rooted cutting, the plant reaches a height of 2 feet and a spread of 3 feet under normal growing conditions in Loxley, Ala. The plant normally grows at the rate of about 6 inches or more per year and reaches a height of 4 feet and spread of 5 feet at maturity while maintaining a dense habit due to the abundant branch development.
Foliage: Alternate, simple, evergreen, elliptic to slightly obovate, almost flat, and varying in size from 2⅛" to 2¾" long and ⅞" to 1⅜" wide. The margins are serrate to crenate, with a petiole ⅜" to 9/16" long. The midrib is prominent on both sides of the leaf and the smaller veins are prominent on the underside. Veins are depressed on the upper side giving a leathery appearance. These upper veins are Yellow-Green Group 146C. The base of the leaf is attenuate to cuneate and the apex is acute. The upper surface of the mature leaf is Yellow-Green Group 147A, glossy, and glabrous. The underside is Yellow-Green Group 146C and matte. The underside veins are Yellow-Green Group 146A. These mature leaf colors are persistent throughout the winter. The immature leaves are tomentulose and pronounced with a light bronze coloration, Yellow-Green Group 152C, which changes to Yellow-Green Group 147A in three to four weeks in Loxley, Ala. The paired foliaceous stipules are 3/16–⅜" long and 1/16–⅛" wide. The upper surface is Yellow-Green Group 145A and the underside is Yellow-Green Group 145B. The stipules are caducous.

In 2000, the date of initial spring growth was March 8, in Loxley, Ala. After the initial spring flush, there was almost continuous slow growth until fall, ending November 8, also in Loxley, Ala. When grown in full sun, the internode length of this plant is ⅜" to ⅝". When grown in light shade, the internode length is ½" to ⅞". As would be expected, a plant grown in the shade results in a taller, less dense plant with larger leaves.

Stems: The young shoots have a reddish pigmentation, Greyed-Purple Group 183D and are tomentulose. The base of the immature petioles are also Greyed-Purple Group 183D. After one or more years, the stems are generally grey (Greyed-Green Group 197B), glabrous and rugose. The pith is solid and uniform.

Flowers: Perfect, single to semi-double, pink, Red-Purple Group 65C front and back, ¾" diameter, fragrant, borne on dense, upright, tomentulose, 3½–4½" high and wide terminal panicles from March to May. As flowers mature they fade to Red-Purple Group 65D and White Group 155C. Each panicle has from 3–9 racemes which have from 1–14 flowers each, resulting in 70 or more flowers per panicle. A mature plant can have 100 or more panicles. The flowers are attached to short pedicels which are ⅛" to ⅜" in length and Yellow-Green Group 146C. The peduncle of each raceme is from ½" to ¾" long and Yellow-Green Group 146C. Each flower has 5–9 petals that are 7⁄16" long and 3⁄16" wide, oblanceolate, and have acute tips. The flower has from 15 to 20 stamens, 3⁄16" long, with anthers Yellow Group 9B. The pollen matures to Yellow Group 9A. The pistil is ¼" long, White Group 155C, and consists of 2 styles which are united and have ciliate margins. In 2001, the blooming period began March 8, in Loxley, Ala. and ended May 2. The self cleaning blooms last 5 to 7 days on the plant in the garden. Some blooms will appear through October in the Southeastern United States.

Fruit: Drupaceous, globose, 1⁄14" to ⅜" in diameter, 1 to 2 seeded. Summer fruit color Yellow-Green Group 144A ripens to Greyed-Purple Group 187A in the fall and persists as Black Group 202A attractively through the winter. Mature seeds are Greyed-Orange Group 163A beneath the pericarp.

Culture: Grows well in a wide range of conditions and tolerates sun to part shade. Grows in nearly any soil type, from moist to very dry and sand to clay. Responds well to mulching and medium applications of fertilizer; prefers ph 6 to 7. Very little pruning is needed. Adaptable to containers and above ground planters. Ideal for coastal regions and warmer parts of the Piedmont. Tolerates wind and salt spray. Propagated with semi-hardwood cuttings in late spring through the summer.

Pests: None observed to date.

I claim:

1. A new and distinct variety of Raphiolepis plant named 'Sopink' as described and illustrated.

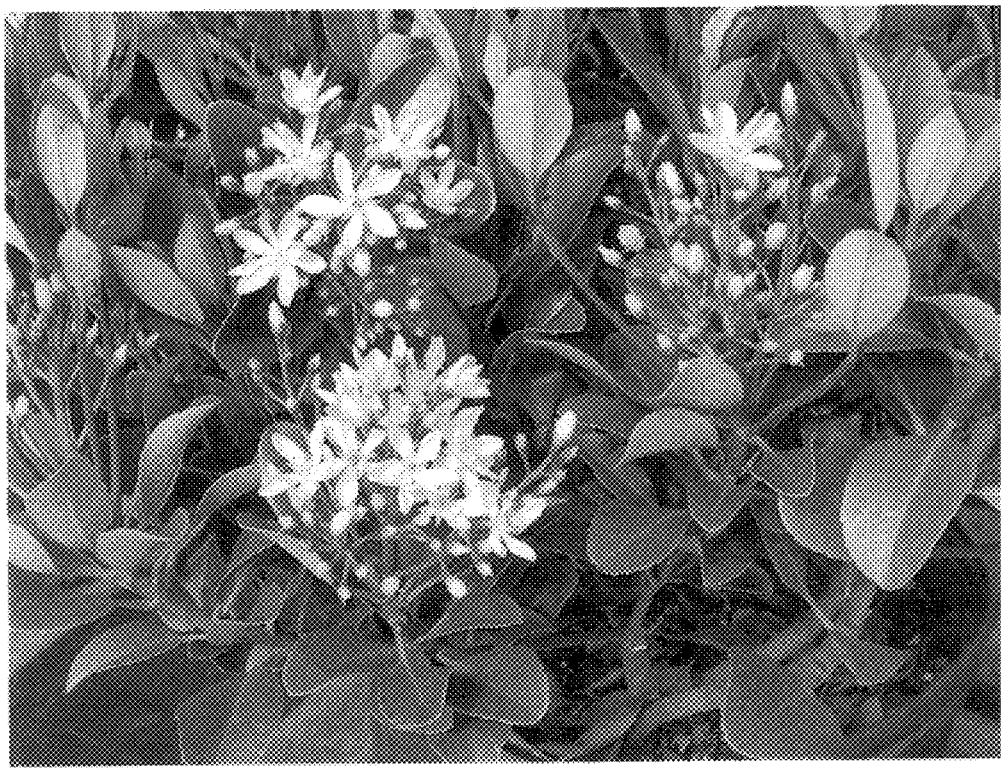
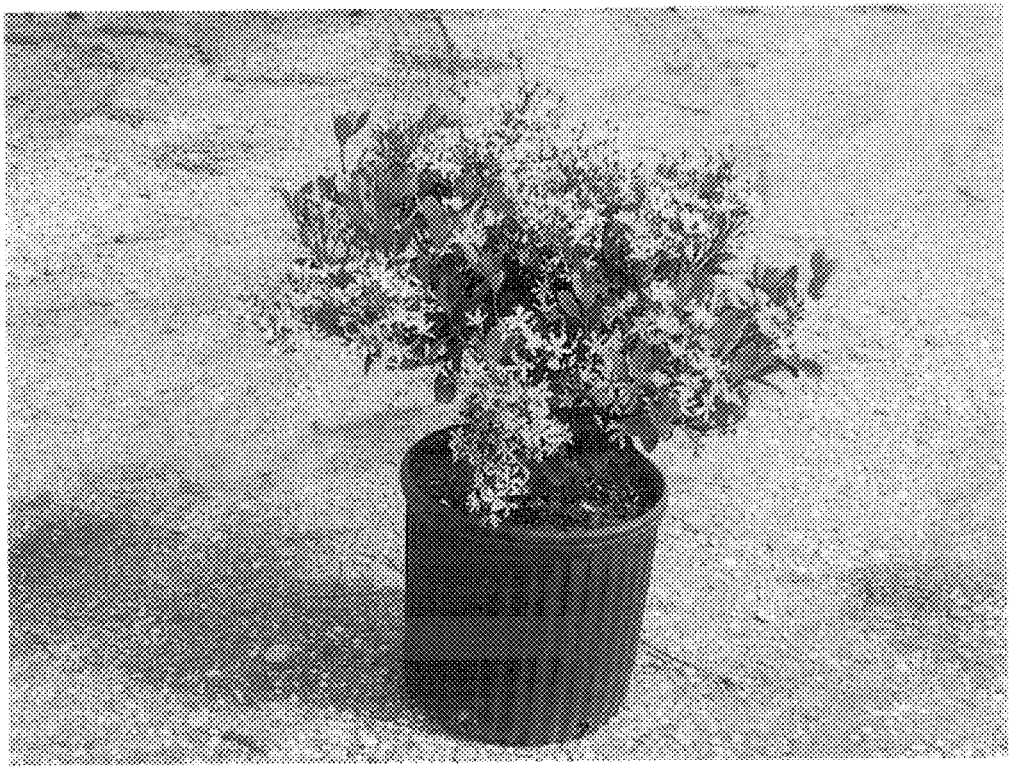

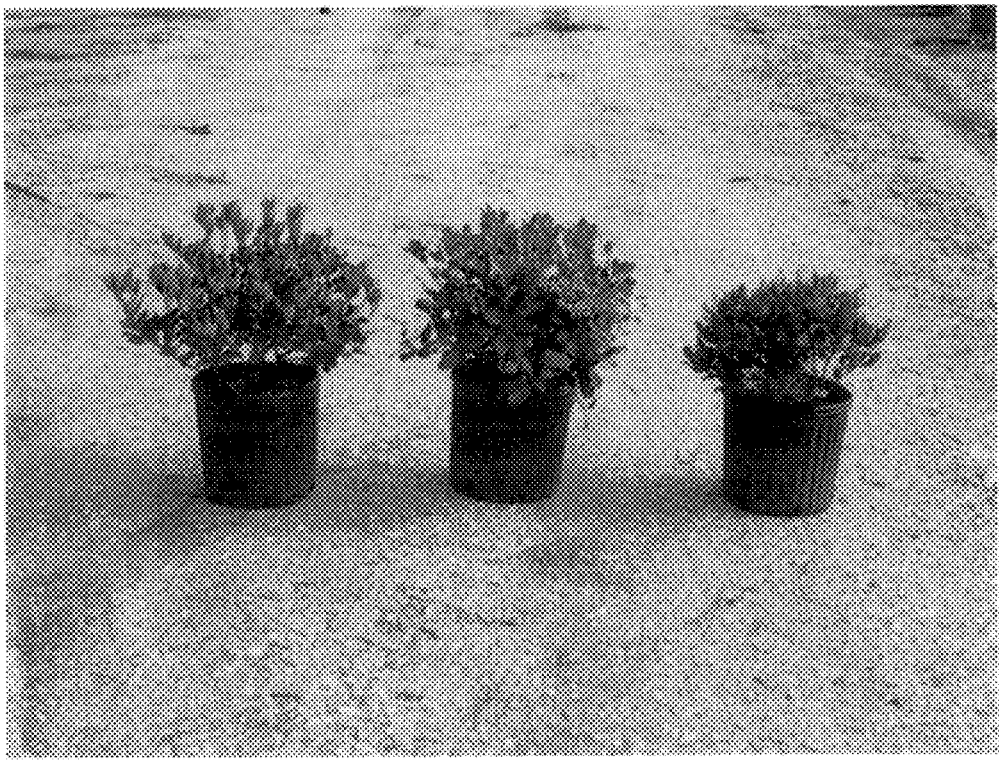
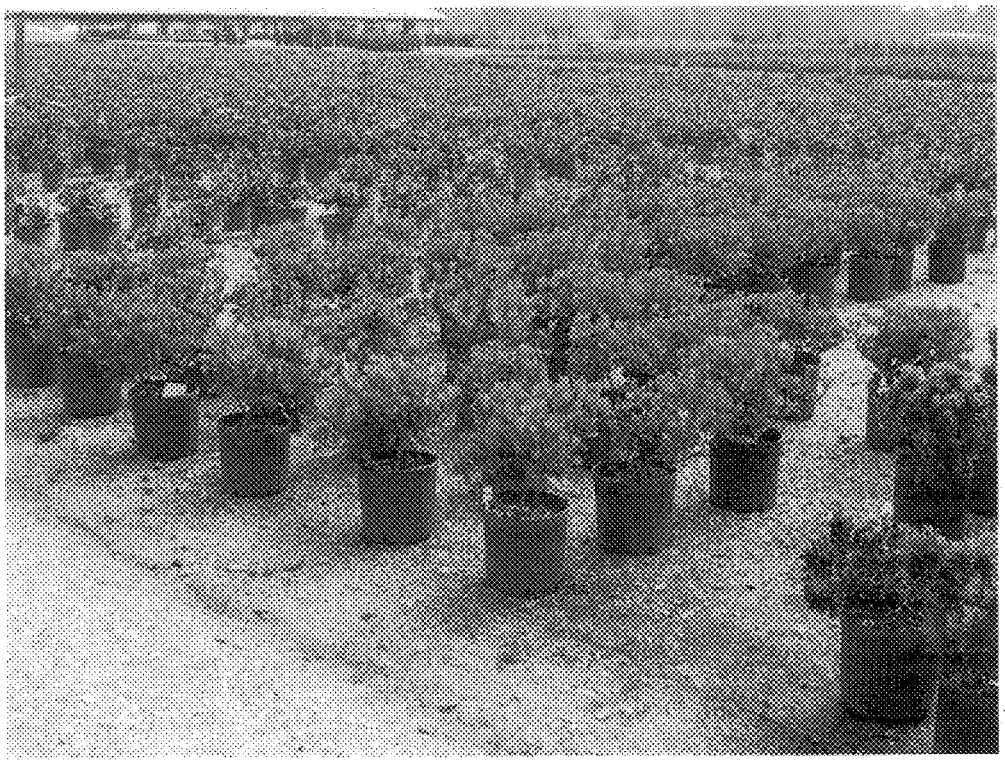

* * * * *